US012805921B2

(12) United States Patent
Stefanov et al.

(10) Patent No.: US 12,805,921 B2
(45) Date of Patent: Nov. 24, 2026

(54) CRYOPROBE

(71) Applicant: AtriCure, Inc., Mason, OH (US)

(72) Inventors: Stefan Stefanov, Ludlow, KY (US); Geni M. Giannotti, Cincinnati, OH (US); Christopher Widenhouse, Mason, OH (US); Jonathon McHale, Mason, OH (US)

(73) Assignee: AtriCure, Inc., Mason, OH (US)

( * ) Notice: Subject to any disclaimer, the term of this patent is extended or adjusted under 35 U.S.C. 154(b) by 1098 days.

(21) Appl. No.: 17/464,968

(22) Filed: Sep. 2, 2021

(65) Prior Publication Data

US 2023/0067890 A1 Mar. 2, 2023

(51) Int. Cl.
*A61B 18/02* (2006.01)
*A61B 18/00* (2006.01)

(52) U.S. Cl.
CPC *A61B 18/0218* (2013.01); *A61B 2018/00434* (2013.01); *A61B 2018/0287* (2013.01); *A61B 2018/0293* (2013.01)

(58) Field of Classification Search
CPC ................ A61B 18/0218; A61B 18/02; A61B 2018/00434; A61B 2018/0287; A61B 2018/0293
See application file for complete search history.

(56) References Cited

U.S. PATENT DOCUMENTS 3,800,552 A 4/1974 Sollami et al.
5,800,488 A 9/1998 Crockett
6,936,045 B2 8/2005 Yu et al.
8,740,891 B2 6/2014 Babkin et al.
8,915,908 B2 * 12/2014 Privitera ................ A61B 18/02 606/21
9,066,713 B2 6/2015 Turovskiy
9,402,676 B2 8/2016 Babkin et al.
2010/0057063 A1 * 3/2010 Arless .................... A61B 18/02 606/21
2011/0009854 A1 * 1/2011 Babkin .................. A61B 18/02 606/23
2011/0245806 A1 10/2011 Patterson
2012/0109117 A1 5/2012 Harp et al.

(Continued)

OTHER PUBLICATIONS https://biomerics.com/engineered-components/complex-extrusions/braided-tubing/, retrieved Aug. 3, 2021.

(Continued)

*Primary Examiner* — Annie L Shoulders
(74) *Attorney, Agent, or Firm* — Dorton & Willis LLP; Ryan Willis

(57) ABSTRACT

Cryogenic devices and methods of using and manufacturing cryogenic devices are disclosed. An exemplary cryogenic device may include an enclosed distal tip delineating a cavity in fluid communication with an egress orifice and an ingress orifice, where at least a portion of an exterior of the distal tip comprises a thermal application zone; an exhaust conduit in fluid communication with the egress orifice; a supply conduit in fluid communication with the ingress orifice, the supply conduit helically extending around at least a portion of the exhaust conduit; and/or a deformable wrap at least partially circumscribing the supply conduit and leaving exposed the thermal application zone.

20 Claims, 5 Drawing Sheets

(56) References Cited

U.S. PATENT DOCUMENTS

| | | | | |
|---|---|---|---|---|
| 2012/0130458 | A1* | 5/2012 | Ryba | A61B 18/02 607/113 |
| 2012/0232543 | A1* | 9/2012 | Sharon | A61B 18/02 606/23 |
| 2012/0283722 | A1* | 11/2012 | Asconeguy | A61B 18/02 606/41 |
| 2012/0289953 | A1* | 11/2012 | Berzak | A61B 18/0218 606/23 |
| 2018/0036166 | A1 | 2/2018 | Burnett et al. | |
| 2018/0310977 | A1* | 11/2018 | Snyder | A61B 18/02 |
| 2020/0085485 | A1* | 3/2020 | Skorich | A61B 18/02 |

OTHER PUBLICATIONS https://biomerics.com/manufacturing/extrusion/multi-lumen/, retrieved Aug. 2, 2021.
https://www.mddionline.com/news/new-extrusion-techniques-advance-catheter-design, retrieved Jun. 25, 2021.
Biomerics brochure, dated Aug. 2019.

* cited by examiner

CRYOPROBE

INTRODUCTION TO THE INVENTION

The present disclosure is directed to cryogenic devices and, more specifically, encompasses cryogenic devices and methods of manufacturing the same, where the cryogenic devices may be used for surgical applications to deliver cooling to one or more tissue locations. In addition, the present disclosure is directed to methods of using cryogenic devices as part of surgical procedures.

Currently, use of cryogenic surgical devices requires a distal application zone reaching therapeutic temperatures while the remainder of the device need not reach or approximate these therapeutic temperatures. Unfortunately, however, most cryogenic surgical devices operate to cool not only the application zone, but also sections of the cryogenic surgical device extending proximally from the distal application zone. And when these proximal sections come into contact with tissue, the tissue can be cooled to temperatures causing unintended temporary or permanent damage. For example, when the pulmonary veins of a human heart are ablated using a conventional cryogenic surgical device, portions of the device may be exposed and contact lung tissue, thereby leading to necrosis or, to a lesser extent, temporary tissue damage.

To avoid inadvertent damage to tissue exposed to portions of the cryogenic surgical device other than the application zone, it is known to insulate the remainder of the device (including sections of the probe proximal to the application zone) using bulky external insulative materials. But these bulky external insulative materials decrease the flexibility of the cryogenic surgical device, increase the cross-section of the cryogenic surgical device inserted into the anatomy, and retard the cryogenic surgical device's ability to conform to tissue having various shapes. Further, bulky cryogenic surgical devices are unable to conform to bends and shape changes in tissue without requiring conforming pressures being applied that are beyond the capabilities of current robotic surgical systems.

In certain cryoprobes commercially available, the temperature of portions of the probe that contact tissue where cryo temperature application is unintended must stay warmer than −10° C. throughout a 120 second cryo application. It is known within the field of cryoablation probes the outer shaft, proximal to the application zone, can get too cold and stick to tissues encountered thereby. This contact with portions of the probe, other than the application zone, can cause temporary or permanent tissue damage if not addressed properly. In addition, it is known that cryo probe shafts may reach temperatures low enough to cause frost bite on the patient's skin where the probe is inserted in-vivo. Currently workarounds to address these problems uniformly fail to address the cryo probe itself, but instead concentrate on spacing between the probe and the unintended contacting tissue using items such as gauze, lap sponges, medicine cups, and chest tubes.

Thus, there is a need in the art for a cryogenic surgical device that includes one or more of: a limited application zone; enhanced flexibility; a smaller cross-section; and, operable to be repositioned using current robotic surgical systems.

In accordance with the present disclosure, exemplary cryogenic devices disclosed herein may be used for ablating cardiac tissue, where each cryogenic device may include a hand piece and a cryogenic probe closed at its distal end and having a central exhaust conduit for discharging spent cryogenic fluid conveyed from the distal end. By way of example, the cryogenic probe may include one or more spiral or coiled conduits configured to direct cryogenic fluid, from a fluid source and through the hand piece, into communication with one or more nozzles positioned proximate a distal end of the cryogenic probe. By way of further example, the cryogenic probe may include a distal end having a stopper or enclosed distal end to inhibit fluid in direct communication with the distal end from leaving and discontinuing direct communication other than through an outlet conduit.

In an exemplary aspect of the present disclosure, exemplary cryogenic devices may include an encased probe circumscribing one or more coiled supply conduits. By way of example, each coiled supply conduit may have coils that are evenly or non-evenly spaced. By way of further example, the spacing of the conduit coils may be static or actively able to be changed during use of the cryogenic device.

In another exemplary aspect, cryogenic surgical devices in accordance with the instant disclosure may include one or more thermocouples to provide feedback concerning the temperatures of the application zone and aspects of the device more proximal than the application zone.

It is a first aspect of the present invention to provide a cryogenic device including an enclosed distal tip delineating a cavity in fluid communication with an egress orifice and an ingress orifice, where at least a portion of an exterior of the distal tip comprises a thermal application zone; an exhaust conduit in fluid communication with the egress orifice; a supply conduit in fluid communication with the ingress orifice, the supply conduit helically extending around at least a portion of the exhaust conduit; and/or a deformable wrap at least partially circumscribing the supply conduit and leaving exposed the thermal application zone.

In a more detailed embodiment of the first aspect, the distal tip may include a plug partially delineating the cavity, wherein the egress orifice and the ingress orifice extend through the plug. In yet another more detailed embodiment, the plug may include a nipple extending away from the distal tip and/or the deformable wrap may circumscribe at least a portion of the nipple. In a further detailed embodiment, the supply conduit may extend through the plug via the ingress orifice and into the cavity. In still a further detailed embodiment, the exhaust conduit may extend at least partially into the plug via the egress orifice. In a more detailed embodiment, the distal tip may include a bulbous cap sealingly connected to the plug to delineate the cavity. In a more detailed embodiment, the supply conduit may extend through the plug via the ingress orifice and within the boundaries the bulbous cap. In another more detailed embodiment, the exhaust conduit may not extend into the cavity. In yet another more detailed embodiment, the cryogenic device may include a first actuator operative to vary spacing between helices of the supply conduit. In still another more detailed embodiment, the cryogenic device may include a second actuator operative to vary spacing between helices of the supply conduit within a second section of the cryogenic probe, where the first actuator is operative to vary spacing between helices of the supply conduit within a first section of the cryogenic probe, where the first and second sections do not overlap.

It is a second aspect of the present invention to provide a cryogenic device including an expansion cavity in fluid communication with an egress orifice and an ingress orifice, where at least a portion of the expansion cavity is in thermal communication with an exterior surface comprising a thermal application zone; an exhaust conduit in fluid communication with the expansion cavity; and/or a supply conduit in fluid communication with the expansion cavity, the supply conduit helically extending around at least a portion of the exhaust conduit proximate the expansion cavity..

In a more detailed embodiment of the first aspect, the expansion cavity may be at least partially delineated by an interface through which the egress orifice and the ingress orifice extend, the interface precluding fluid communication between the exhaust conduit and the supply conduit on a first side and allowing fluid communication between the exhaust conduit and the supply conduit on a second side. In yet another more detailed embodiment, the expansion cavity may be located at a distal tip of the cryogenic device. In a further detailed embodiment, the expansion cavity may be at least partially delineated by a bulbous projection. In still a further detailed embodiment, the supply conduit may helically extend around at least a portion of the exhaust conduit within two centimeters of the bulbous projection.

It is a third aspect of the present invention to provide a cryogenic device including an exhaust conduit in fluid communication with an expansion cavity; a supply conduit in fluid communication with the expansion cavity, the supply conduit helically extending around at least a portion of the exhaust conduit; and/or an actuator operatively coupled to the supply conduit, the actuator repositionable along a range of travel to vary spacing between helices of the supply conduit, where varying the spacing between the helices of the supply conduit is operative to change the flexibility of the cryogenic device where the supply conduit helically extends around at least the portion of the exhaust conduit.

It is a fourth aspect of the present invention to provide a method of operating a cryogenic surgical device including positioning a thermal application zone of an enclosed distal tip of a cryogenic surgical device proximate a target tissue, the distal tip delineating a cavity in fluid communication with an egress orifice and an ingress orifice; cooling the thermal application zone of the distal tip by supplying a cryogenic fluid through the ingress orifice from a supply conduit helically extending around at least a portion of an exhaust conduit while insulating at least a portion of the supply conduit using a deformable wrap at least partially circumscribing the supply conduit and leaving exposed the thermal application zone, the exhaust conduit in fluid communication with the egress orifice; warming the distal tip by restricting flow of the cryogenic fluid through the exhaust conduit; and/or removing the distal tip from proximate the target tissue.

In a more detailed embodiment of the fourth aspect, positioning the thermal application zone of the enclosed distal tip of the cryogenic surgical device proximate the target tissue may include placing the distal tip in direct contact with the target tissue. In another more detailed embodiment, positioning the thermal application zone of the enclosed distal tip of the cryogenic surgical device proximate the target tissue may include operating an actuator to vary spacing between helices of the supply conduit, where varying the spacing between the helices of the supply conduit is operative to change the flexibility of the cryogenic device where the supply conduit helically extends around at least the portion of the exhaust conduit. In yet another more detailed embodiment, positioning the thermal application zone of the enclosed distal tip of the cryogenic surgical device proximate the target tissue may include placing the distal tip proximate at least one of cardiac tissue and nerve tissue.

DETAILED DESCRIPTION

The exemplary embodiments of the present disclosure are described and illustrated below to encompass exemplary cryogenic devices and, more specifically, encompasses cryogenic devices and methods of manufacturing the same, where the cryogenic devices may be used for surgical applications to deliver cooling to one or more tissue locations. In addition, the exemplary embodiments are directed to methods of using cryogenic devices as part of surgical procedures. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
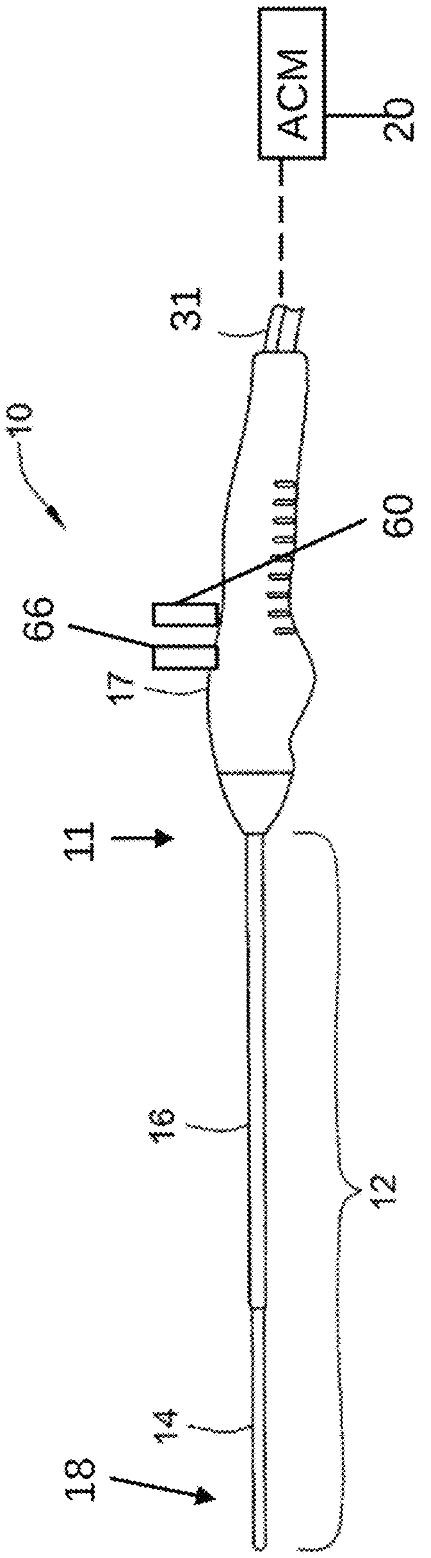
FIG. 1 is a hybrid profile view and a schematic of an exemplary cryogenic surgical system in accordance with the instant disclosure.

Referencing FIG. 1, an exemplary cryogenic surgical system 10 in accordance with the instant disclosure may comprise a cryogenic surgical device 11 in fluid communication with a cryogenic module (ACM) 20. In exemplary form, the ACM 20 may supply cryogenic fluid to the surgical device 11 via one or more fluid lines 31. In addition, the ACM 20 may capture spent cryogenic fluid routed through the surgical device 11 as a means to capture and potentially reuse the cryogenic fluid. Alternatively, the ACM 20 may allow for venting of spent cryogenic fluid having already flown through the surgical device 11 or, in addition, the surgical device 11 may provide venting of spent cryogenic fluid without first routing the fluid back to the ACM.

In exemplary form, the fluid lines 31 may be part of the surgical device 11 and at least one of these lines may be utilized to convey cryogenic fluid from the ACM 20, through a handle 17 of the surgical device, and into communication with a cryogenic probe 12. It should be noted, however, that an exemplary surgical device 11 in accordance with the instant disclosure need not include the handle 17. By way of example, the cryogenic probe 12 may include different sections 14, 16 that exhibit different flexibilities. As used herein, “flexible” or “flexibilities” may describe a property of a component that is elastically and/or plastically deformable when subject to forces consistent with normal, intended use. By way of further example, the proximal or first section 16 may be distal to the handle 17 and proximal with respect to a second distal section 14, where the distal section 14 includes a distal tip 18.

Figure 2:
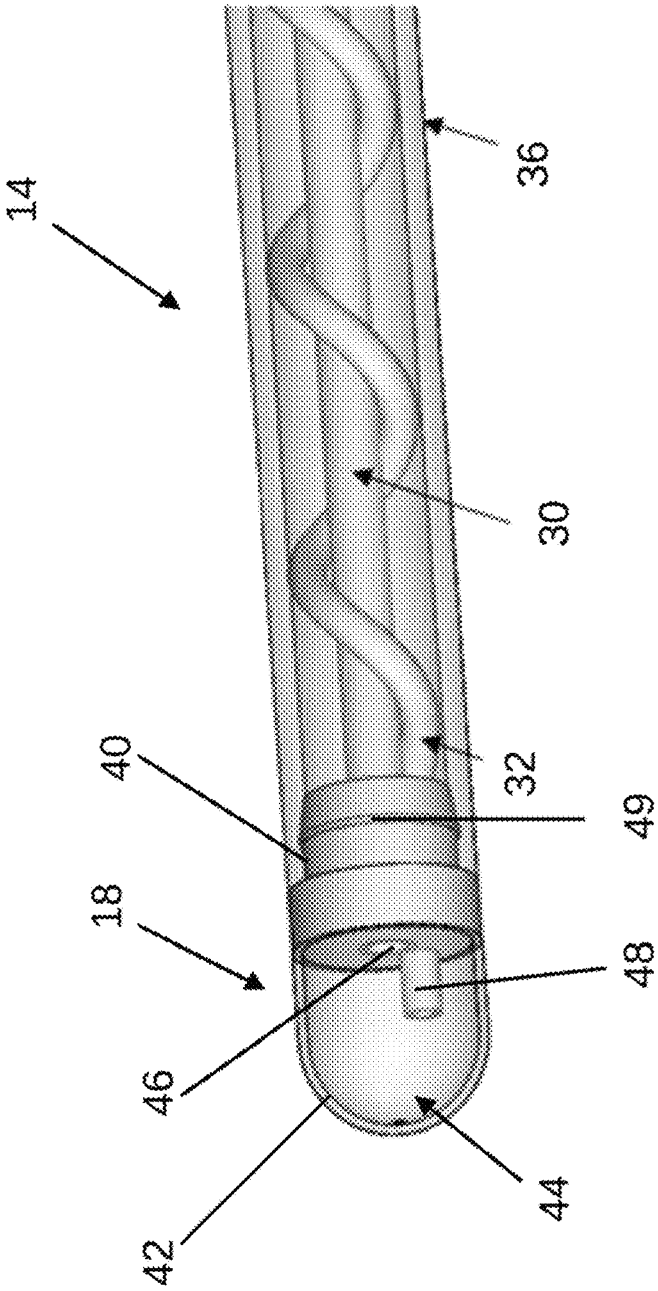
FIG. 2 is a profile, cut away view of an exemplary distal section of a cryogenic surgical device in accordance with the instant disclosure.
Figure 3:
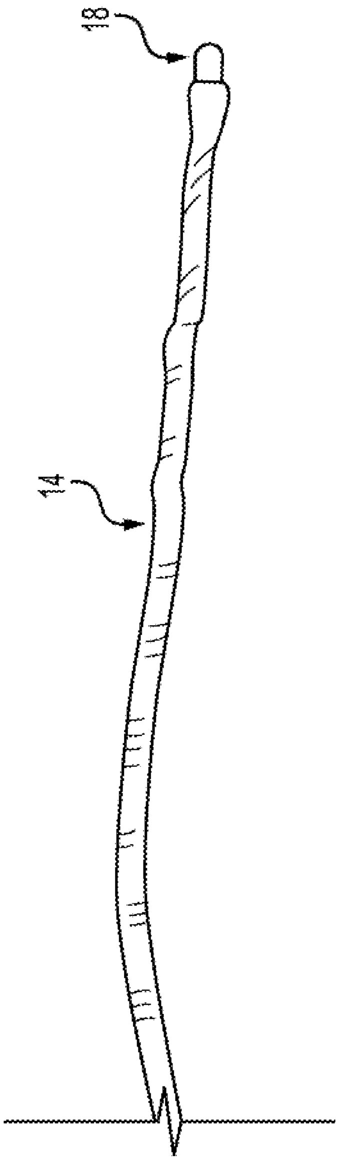
FIG. 3 is a profile view of an exemplary distal section of the cryogenic surgical device of FIG. 2.
Figure 4:
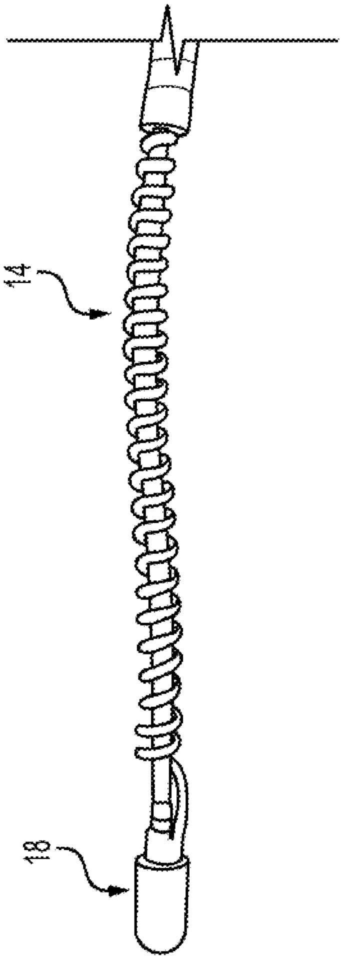
FIG. 4 is a profile view of the exemplary distal section of the cryogenic surgical device of FIG. 3 with a portion of the flexible covering removed.

Referring to FIG. 2, an exemplary distal section 14 in accordance with the instant disclosure may include an exhaust conduit 30 utilized to carry spent fluid from the distal tip 18, where the exhaust conduit may be circumscribed along a majority or minority of its length by a helically shaped conduit 32 in communication with one or more of the fluid lines 31. In exemplary form, the exhaust conduit 30 may be centrally located longitudinally along the distal section 18 and may have a circular or non-circular cross-section. More specifically, the cross-section of the exhaust conduit 30 may be uniform or non-uniform along its longitudinal length. By way of example, the exhaust conduit 30 may increase in cross-section from distal to proximal to accommodate for further expansion of the spent fluid. In addition, the exhaust conduit 30 may increase in thickness from proximal to distal to accommodate higher pressures of spent fluid nearer the distal tip 18.

In the example embodiment illustrated in FIG. 2, the exhaust conduit 30 may be generally concentrically disposed within the helically shaped supply conduit 32 and/or the supply conduit 32 may be disposed generally concentrically within the probe 12 (FIG. 1). As used herein, “concentric” may describe components which are arranged so that they have a common center point. For example, in some embodiments including helically shaped conduits (e.g., supply conduit 32), the center of the helix may be arranged concentrically with the center of the exhaust conduit 30. In alternative example embodiments, the conduits 30, 32 may be disposed within one another and/or within the probe 12 non-concentrically. In some example embodiments, the cryogenic fluid flowing to the distal section 18 may be substantially warmer than the spent cryogenic fluid flowing from the distal section 18. Accordingly, disposing the exhaust conduit 30 generally within the supply conduit 32 (concentrically or non-concentrically) may allow the supply conduit 32 and/or the relatively warmer cryogenic fluid therein to insulate tissues near the probe 12 from the cold spent cryogenic fluid in the exhaust conduit 30.

By way of example, the helically shaped conduit 32 may be fabricated from various materials including, without limitation, metals such as stainless steel and aluminum, and plastics including polyethylene, high density polyethylene, polyurethane, polyester block amides such as Pebax elastomers and Vestamid polymers, polytetrafluoroethylene (PTFE), nylon, and/or other polymers (elastomers, thermoplastics). It is further within the scope of the disclosure that a helically shaped polymer conduit 32 may be fiber reinforced using braiding or stranding, where the fibers comprise various materials including, without limitation, high density polyethylene, polyesters (such as polyethylene terephthalate), and metals such as stainless steel, titanium, and non-stainless steel. By way of further example, the cross-sectional area (measured from the inside) of the helically shaped conduit 32 may range from about $1.39\times10^{-3}$ square inches to about $4.30\times10^{-3}$ square inches in order to provide the desired flow rate for the fluid. The longitudinal spacing between respective helices of the conduit 32 may range between 0 to 2 inches. As referenced hereafter, the longitudinal spacing between the helices may vary actively within a given probe length, or may vary across probe options, such as later exemplary embodiments disclosed herein. In any event, the helically shaped conduit 32 terminates proximate the distal tip 18.

By way of further example, the exhaust conduit 30 may be fabricated by various materials including, without limitation, metals such as stainless steel and aluminum, and plastics including polyethylene, high density polyethylene, polyurethane, polyester block amides such as Pebax elastomers and Vestamid polymers, polytetrafluoroethylene (PTFE), nylon, and/or other polymers (elastomers, thermoplastics). It is further within the scope of the disclosure that a polymer exhaust conduit 30 may be fiber reinforced using braiding or stranding, where the fibers comprise various materials including, without limitation, high density polyethylene, polyesters (such as polyethylene terephthalate), and metals such as stainless steel, titanium, and non-stainless steel. By way of further example, the cross-sectional area (measured from the inside) of the exhaust conduit 30 may range from about $1.39\times10^{-3}$ square inches to about $4.90\times10^{-2}$ square inches in order to provide the desired flow rate for the fluid.

Figure 5:
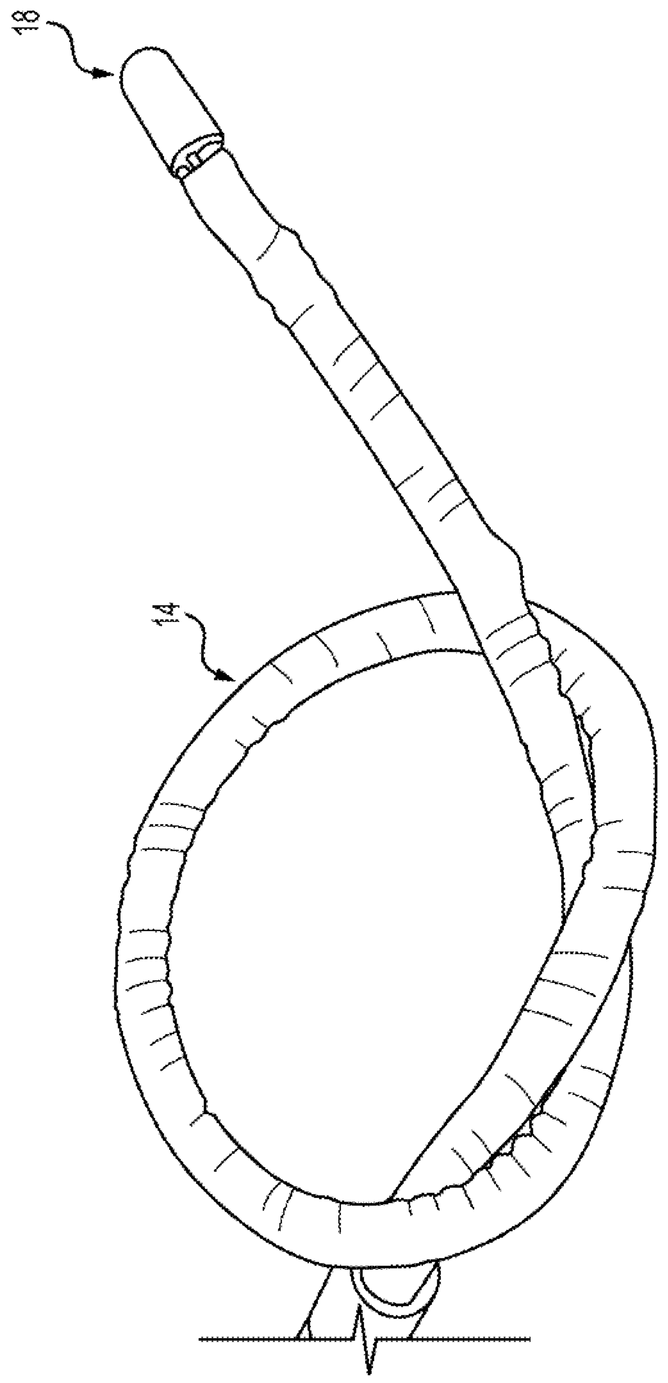
FIG. 5 is a profile view of the exemplary distal section of the cryogenic surgical device of FIG. 3 displaying its flexibility.

In exemplary form, the exhaust conduit 30 and the helically shaped conduit 32 may be circumscribed by a flexible covering 36. By way of example, the flexible covering 36 may be fabricated from silicone, polyurethane, polytetrafluoroethylene (PTFE), nylon, and/or other polymers (elastomers, thermoplastics) and may be processed to conform to the exterior shape of the helically shaped conduit 32 to form a corrugated exterior (see FIG. 5) using techniques, such as, without limitation thermal shrinking, molded, thermoformed, retention sleeve, or otherwise formed to cinch around the plug 40. For example, the flexible covering 36 may also circumscribe a nipple 49 extending proximally from the plug 40 in order to provide the flexible covering with a distal most foothold. In this manner, the flexible covering 36 may insulate at least a portion of the supply conduit and leave exposed the thermal application zone of the distal tip 18.

Figure 6:
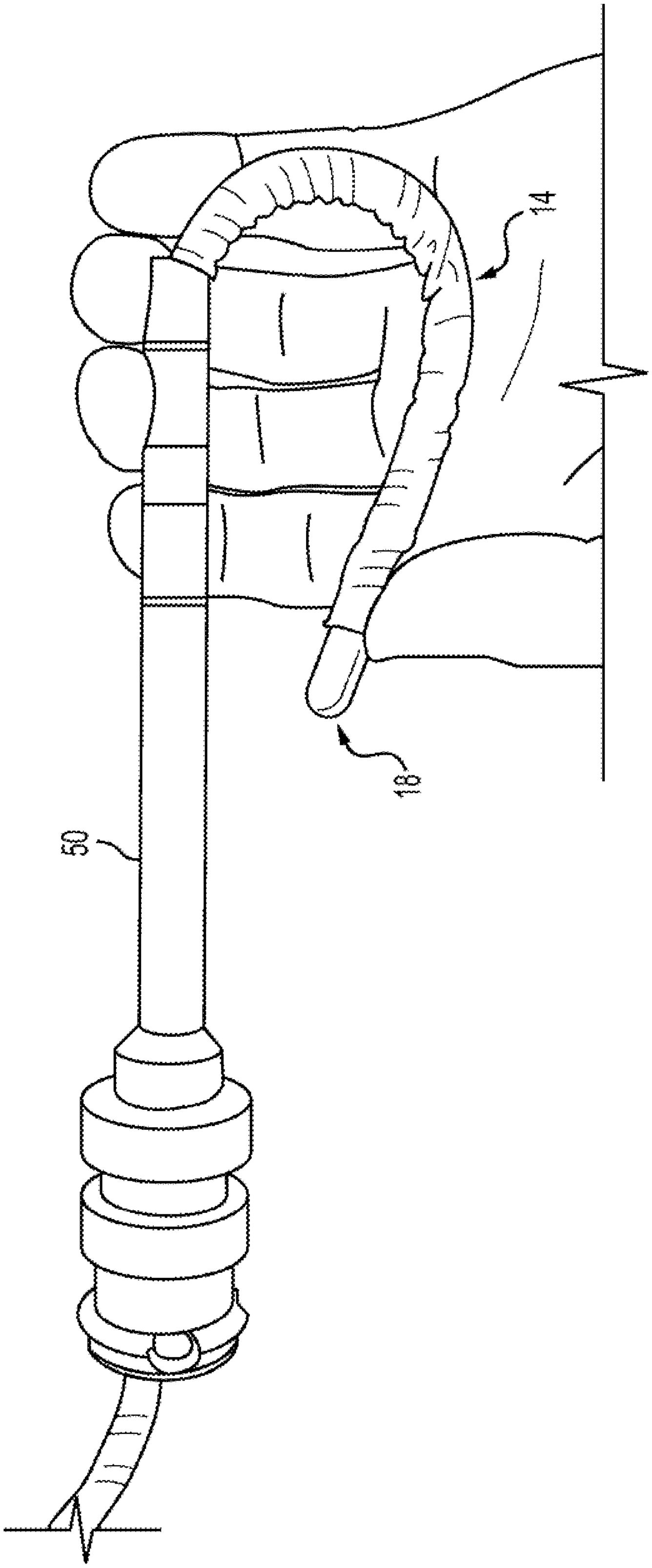
FIG. 6 is a profile view of the exemplary distal section of the cryogenic surgical device of FIG. 3 inserted through an eight millimeter trocar.

By way of still further example, an exemplary distal section 14 in accordance with the instant disclosure may include a sealed distal tip 18 that includes a proximal plug 40 sealingly connected to a bulb 42. For example, a maximum widthwise dimension of the plug 40 and bulb 42 may be eight millimeters so as to allow the distal tip 18 to pass through an eight millimeter trocar 50 (see FIG. 6). In exemplary form, an interior cavity 44 at the distal tip 18 is delineated in part by a proximal planar surface of the plug 40 and a concave interior surface of the bulb. In exemplary form, the exterior of the bulb 42 is generally bulbous in shape, however any number of shapes may be achieved by using any number of combinations of variously shaped plugs 40 and bulbs 42. By way of further example, the plug 40 may include a convex or concave proximal surface that sealingly engages, without limitation, a cylindrical, spherical, conical, or other shaped bulb 42. For example, the proximal plug 40 may delineate a through orifice 46 in fluid communication with the exhaust conduit. In exemplary form, the through orifice 46 may be unitary or may be multiple, as well as potentially varying or being uniform in cross-section. As depicted in FIG. 2, the through orifice 46 comprises a single, cylindrically shaped opening in direct communication with an inlet of the exhaust conduit 30 so that all of the fluid occupying the distal tip 18 must egress through the orifice 46. It should also be noted that the through orifice 46 may be centered longitudinally along the length of the plug 40 or may be offset from the longitudinal center. Moreover, in instances where the through orifice 46 is multiplied, the through orifices may be symmetrically distributed around the longitudinal center of the plug 40 or may be asymmetrically distributed with respect to the longitudinal center of the plug.

In addition to delineating the through orifice 46, the proximal plug 40 may also include a nozzle 48 in fluid communication with the inlet fluid line 32. By way of example, the fluid line 32 may be routed at least partially through the proximal plug and, in further exemplary form, may extend completely through the plug and extend into the interior cavity 44. Alternatively, the proximal plug 40 may include a separate supply opening that is in communication with the fluid line 32 to convey fluid from the line, through the plug, an into the interior cavity 44. In any event, when fluid exits the nozzle 48, the fluid is delivered into the interior cavity and into thermal communication with the interior surfaces of the proximal plug 40 and the bulb 42.

As mentioned, fluid conveyed into the interior cavity 44 occupies the interior cavity prior to exiting through the through orifice 46. In exemplary form, the fluid may be introduced at a pressure higher than that within the interior cavity 44, thereby allowing the fluid to expand and, where the fluid includes a liquid component, totally or partially vaporizing the fluid. More specifically, if the fluid introduced to the interior cavity 44 is completely a gas, the gas may be supplied at a higher pressure so as to allow the gas to expand at a lower pressure within the interior cavity, which resultingly causes a lowering of temperature of the gas occupying the interior cavity, thereby convectively cooling the bulb 42 and creating an application zone on the exterior of the bulb. In further exemplary form, if the fluid introduced to the interior cavity 44 is at least partially a liquid, at least a portion of the liquid may boil, which resultingly causes a lowering of temperature of the gas and any liquid occupying the interior cavity, thereby convectively cooling the bulb 42 and creating an application zone on the exterior of the bulb. Those skilled in the art are familiar with delivery of fluids to an enclosed area and changing the conditions of the fluids to cause a reduction in temperature of the fluids within an enclosed area.

By way of example, a higher pressure fluid entering the interior cavity 44 creates a driving force effectively pushing fluid out of the interior cavity, through the orifice 46 of the plug 40 and into communication with an interior of the exhaust conduit 30. However, the magnitude of this driving force may be changed by varying the conditions downstream from the through orifice 46. In exemplary form, the exhaust conduit 30 and elements downstream therefrom may include active valves to vary the backpressure within the exhaust conduit. In further exemplary form, the exhaust conduit 30 may be in closed fluid communication with one or more active valves within the ACM 20 to allow the fluid to be vented, collected in a dedicated receptacle, or recycled for delivery through the fluid line 32. In an exemplary circumstance where the fluid is to be vented, one or more valves within the ACM 20 may be closed, fully open, or partially open to vary the backpressure within the exhaust conduit. For example, if one or more valves within the ACM, in fluid communication with the exhaust conduit 30, is operative as a vent and is fully closed, eventually the backpressure within the exhaust conduit will roughly equate to the pressure of the fluid within the bulb 42. As a result, the driving force will be reduced and fluid within the bulb 42 will stagnate and operate to increase the pressure within the bulb, thus increasing the temperature of the fluid within the bulb and correspondingly increase the temperature of the exterior of the bulb. As a result, by increasing the backpressure with respect to the exhaust conduit 30, the exemplary distal tip may be thawed or actively heated.

Alternatively, in a case where one or more valves is acting as a vent and at least partially open, the backpressure within the exhaust conduit 30 is below a maximum pressure (e.g., where the valve(s) is closed as discussed previously). This partially opened valve may result in a condition where the driving force is reduced below a maximum in comparison to a condition where the valves are fully open and the backpressure within the exhaust conduit is at a relative minimum. But venting is not the only option for spent fluid exiting the distal tip 18.

As mentioned, the ACM 20 may be in fluid communication with a fluid receptacle (not shown) for accumulating spent fluid. This fluid receptable may include or be in communication with a compressor that may draw fluid through the exhaust conduit 30 at a negative pressure (e.g., suction) and deliver the fluid into a pressurized fluid receptable. In addition, such a compressor may operate to compress the fluid within the pressurized fluid receptable, where the fluid may be stored under pressure in a liquid, a gas, or a combination thereof. In such a circumstance, the pressurize fluid receptable may be utilized as a fluid source for supply of fluid from the ACM 20.

Figure 7:
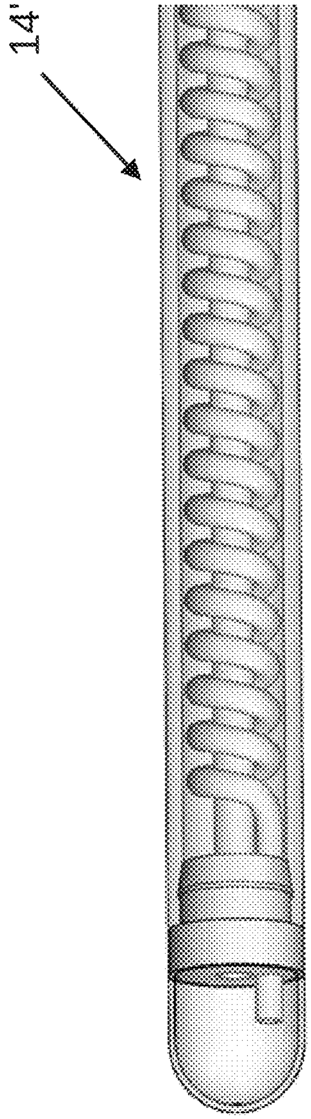
FIG. 7 is a profile, cut away view of a first alternate exemplary distal section of a cryogenic surgical device in accordance with the instant disclosure.
Figure 8:
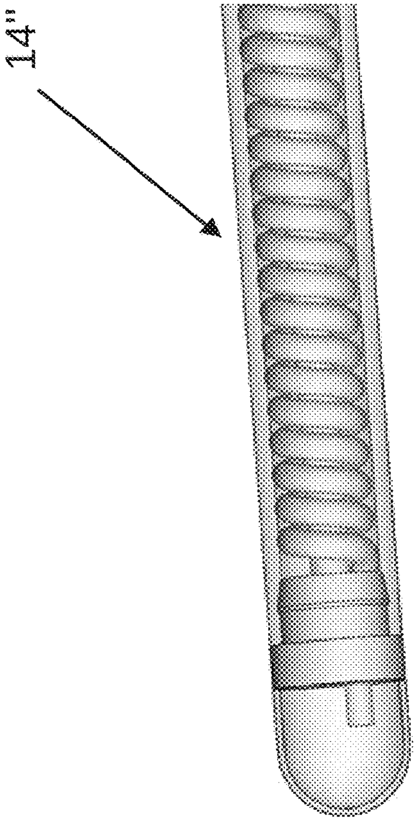
FIG. 8 is a profile, cut away view of a second alternate exemplary distal section of a cryogenic surgical device in accordance with the instant disclosure.

Turning to FIGS. 7 and 8, a cryogenic surgical device 11 in accordance with the instant disclosure may include a distal section 14 where the spacing between the helices of the helically shaped conduit 32 varies. For example, the distal section 14' of FIG. 7 exhibits helices spaced more closely that the distal section 14 of FIG. 2. In this manner, the corresponding flexibility of the distal section 14' of FIG. 7 would generally be less than that of the distal section 14 of FIG. 2. Moreover, by way of further example, the distal section 14" of FIG. 8 exhibits helices spaced more closely that the distal sections 14, 14' of FIGS. 2 and 7. In this manner, the corresponding flexibility of the distal section 14" of FIG. 8 would generally be less than that of the distal sections 14, 14' of FIGS. 2 and 7. While the spacing of the helices depicted in FIGS. 2, 7, and 8 may be relatively static (obviously changing when the device section is bent), it is also within the scope of this disclosure to actively vary the spacing of the helices (other than device section bending) in order to provide the device sections with greater or lesser flexibility (or rigidity) depending upon the intended target tissue or any other consideration known to one using the cryogenic surgical device 11.

Turning back to FIG. 1, an exemplary handle 17 may include an actuator 60 operatively coupled to at least one helically shaped conduit 32. By way of example, the actuator 60 may be repositionably mounted to the handle 17 and have a predefined length of travel with respect to the handle. In this manner, a user grasping the handle 17 may reposition the actuator along its length of travel to vary the stiffness or flexibility of one or more of the sections 14, 16, depending upon where and to what helically shaped conduit the actuator is operatively coupled to. By way of further example, the actuator 60 may be operatively coupled to a portion of a helically shaped conduit 32 located in the distal or proximal sections. By repositioning the actuator 60 distally with respect to the handle 17, the actuator would operate to compress the helically shaped conduit 32 so as to change the spacing of the helices from the spacing depicted in FIG. 7 to the spacing depicted in FIG. 8. Doing so would effectively render the section less flexible. In other words, the section 14' depicted in FIG. 7 is more flexible than the section 14" depicted in FIG. 8 because the frequency of the helices is greater per unit length. Alternatively, by repositioning the actuator 60 proximally with respect to the handle 17, the actuator would operate to expand the helically shaped conduit 32 so as to change the spacing of the helices from the spacing depicted in FIG. 7 to the spacing depicted in FIG. 2. Doing so would effectively render the section more flexible. In other words, the section 14' depicted in FIG. 7 is less flexible than the section 14 depicted in FIG. 2 because the frequency of the helices is greater per unit length.

It is also within the scope of the disclosure that the exemplary handle 17 may include a second actuator 66 operatively coupled to the same or at least a second helically shaped conduit 32. By way of example, this second actuator 60 may be repositionably mounted to the handle 17 and have a predefined length of travel with respect to the handle. In this manner, a user grasping the handle 17 may reposition the second actuator 66 along its length of travel to vary the stiffness or flexibility of one or more of the sections 14, 16. In exemplary form, the first actuator 60 may be used to vary the spacing of the helices in the distal section 14, whereas the second actuator 66 may be used to vary the spacing of the helices in the proximal section 16. In yet a further alternative embodiment, the first and second actuators 60, 66 may be mounted to separate helically shaped conduits 32 within the same section 14, 16. In this manner, the actuators 60, 66 allow for fine tuning of the flexibility within a section itself. For example, a distal most portion of the distal section 14 may be configured to have increased flexibility, whereas a proximal most portion of the distal section may be configured to have decreased flexibility.

The foregoing cryogenic surgical device 11 and those exemplary variations disclosed herein address needs in the art for insulating portions of the device unintended as an application zone, as well as providing a probe having increased flexibility and a smaller outer profile. In exemplary form, the exemplary surgical devices disclosed herein provide improved insulation to the end user and patient, preventing damage to unintended tissue that may be surrounding the targeted freeze area.

In addition, the foregoing cryogenic surgical device 11 and those exemplary variations disclosed herein are more flexible than the current commercial offerings and allow for grasping and manipulation with robotic graspers.

Some exemplary devices may be used during surgical categories such as Cardio Thoracic, General Thoracic, Orthopedic; more specifically some exemplary devices may be used for cardiac ablation, cryogenic nerve block, dermal freezing, and/or tumor ablation. Additionally, some exemplary devices may be used with the following surgical procedural approaches: Open, Minimally Invasive Surgery (MIS), Video-Assisted Thoracoscopic Surgery (VATS), and Robotic.

Exemplary methods of using a cryogenic surgical device 11 according to at least some aspects of the present disclosure is discussed hereafter. As a prefatory matter, a supply of cryogenic fluid needs to be established from a static location or from a portable fluid holding container. By way of example, in an exemplary context of using nitrous oxide as the cryogenic fluid, a portable fluid holding container of liquified nitrous oxide may be fluidically connected to an ACM 20 that is itself fluidically connected to the cryogenic surgical device 11.

In exemplary form, the ACM 20 may be intended for use in the cryosurgical treatment of cardiac arrhythmias. The ACM 20 may include an electro-mechanical cryogenic surgical unit (that may include controls, displays, indicators, and associated programmed logic or circuitry) that delivers a cryogenic fluid (e.g., nitrous oxide ($N_2O$)) to a cryogenic surgical device 11 under conditions to cool an active region of the device 11 that is operative to ablate tissue coming into contact with the active region while the cryogenic fluid flows through the device 11, which in exemplary form allows an operator to create lines of ablation through tissue such as, without limitation, cardiac tissue. The ACM 20 may further include a cryogenic fluid holding container, a cryogenic fluid supply line in fluid communication (or selective fluid communication) with the holding container, a cryogenic fluid exhaust line, a holding container heater, and a manual switch allowing control of delivery of cryogenic fluid from the holding container and to the cryogenic surgical device 11. In exemplary form, ACM 20 provides controlled delivery of cryogenic fluid to the cryogenic surgical device 11 to allow tissue lesion formation below −40° C., with typical operating ranges between −50° C. to −70° C.

Cryogen conditions may be regulated and/or verified. In exemplary form, the portable fluid holding container may have a heater blanket covering the tank this is operative to add heat to the container to control the internal pressure, which in exemplary form may range between approximately 700 psi (−17° C.) and 850 psi (−23° C.). By way of example, the ACM 20 may provide visual feedback regarding the pressure and temperature of the container, which is updated in real-time. To the extent heat is needed to reach the proper pressure, a green light may illuminate as part of the ACM 20 to signify that the cryogen tank pressure is within a predetermined operating range.

A user may activate the ACM 20 to deliver pressurized cryogenic fluid via a supply line to the cryogenic surgical device 11. By way of example, the ACM 20 may deliver pressurized cryogenic fluid at approximately 725 psi to the inlet connections (e.g., fluid lines 31) of the cryogenic surgical device 11 so that just prior to reaching the distal tip 18, the pressure of the cryogenic fluid is between 500 and 725 psi.

Cryogen may be delivered to the cryogenic surgical device 11. Upon initial delivery of cryogenic fluid into the distal tip 18, the cryogenic fluid expands to approximately atmospheric pressure (14.7 psi). The backpressure of the spent cryogen may be monitored and/or regulated. In exemplary form, as more cryogenic fluid enters the distal tip 18 and spent cryogenic fluid accumulates, backpressure begins to form and may be regulated to reach a steady state backpressure of approximately 52 psi, which corresponds to an ablation tip temperature of approximately −65° C. It should be noted, however, that using the thermal application zone of the distal tip 18 to ablate tissue may commence after the temperature of the distal tip 18 reaches a predetermined value, which may be above the steady-state temperature, including, without limitation, −40° C.

An ablation cycle may be commenced. Upon the distal tip 18 reaching the predetermined ablation temperature, the ACM 20 may perform an ablation cycle where the thermal application zone of the distal tip 18 is maintained at or below the predetermined ablation temperature for a predetermined time, such as, without limitation, 120 seconds.

A defrost (e.g., warming) cycle may be commenced. In exemplary form, upon completion of the ablation cycle, the ACM 20 may activate the defrost cycle. By way of example, the defrost cycle may include blocking the flow of exhausted cryogenic fluid coming from the cryogenic surgical device 11 while continuing to supply cryogenic fluid to the cryogenic surgical device 11. Eventually, the cryogenic fluid within the cryogenic surgical device 11 is all at the same pressure and temperature, such as, without limitation, approximately 800 psi (corresponding to a distal tip 18 temperature of approximately 10° C.). Notably, various exemplary cryogenic surgical devices 11 according to at least some aspects of the present disclosure may be constructed to withstand pressures expected during defrost cycles, which may be higher than pressures expected during freezing cycles. The ACM 20 monitors the temperature at the distal tip 18 using a thermocouple and, upon reaching a predetermined defrost temperature, discontinues inlet flow of cryogenic fluid to the cryogenic surgical device 11 while allowing venting of the exhausted cryogenic fluid, eventually increasing the temperature and decreasing the pressure of the cryogenic surgical device 11 to atmospheric conditions.

Post termination of the defrost cycle, the ACM 20 may be activated again to restart a freezing and defrost cycle. Alternatively, a procedure termination sequence may be initiated where connections between the cryogenic surgical device 11 and tank are discontinued and the ACM 20 is deactivated.

Some exemplary cryogenic surgical devices 11 may also be used in an application for cryoanalgesia. Cryoanalgesia, or freezing of nerves, uses extreme cold to ablate peripheral nerves and create a temporary yet fully recoverable loss of sensory nerve function. Cryoanalgesia causes axonotmesis, a level of nerve injury according to Seddon's classification in which the axons and the myelin are disrupted but at least some of the surrounding tubular structures, such as the endoneurium, perineurium, fascicle, and/or epineurium, remain intact. The ensuing Wallerian degeneration, a process in which the entire length of the nerve segment distal to the cryoanalgesia site (cryolesion) is dismantled, takes approximately 1 week. Regeneration of the nerve begins from the proximal segment and continues at an average rate of 1-3 mm/day, following the intact structural components until the tissue is reinnervated. This process can take weeks to months depending on how significant the cryolesion is on the tissue. Because it preserves the structure of the nerve, cryoanalgesia has not been associated with development of neuromas.

Local analgesia to a nerve (e.g., intercostal nerve) is intended for managing pain due to the incision, any surgical muscle disruption, discomfort from nerve impingement by the surgical equipment (e.g., retractors) and surgical retainers (e.g., sutures), and for any opening created by a tube or trocar site. In exemplary form, one exemplary process comprises cryoanalgesia for post-thoracotomy pain that includes cryoablation of the intercostal nerves. Cryoablation attempted at temperatures not cold enough, for example, warmer than −20° C., will produce only transient nerve conduction block with a return to sensation upon tissue thawing, whereas temperatures too cold, for example colder than −100° C., can induce permanent nerve damage. When placed against tissue, such as the pleura or intercostal nerve, an ice ball may form around the thermal application zone of the distal tip 18 of the cryogenic surgical device 11 and heat withdrawal may penetrate the tissue by several millimeters to create the cryolesion. In addition to the cryogenic surgical device 11 temperature, the extent of the cryolesion may depend on a number of other factors, including the size and material of the cryogenic surgical device 11, the duration of the freeze, the rate of freeze, the thaw rate, and the number of freeze-thaw cycles. What follows is an exemplary procedure for conducting a cryoanalgesia responsive to a thoracotomy that is effective for pain management and may be applied to any nerve within an animal body.

It may be recommended to perform the cryoablation procedure as early as possible in the procedure, such as prior to or immediately following creation of the thoracotomy. The target nerve, such as an intercostal nerve, may be located in the incisional intercostal space (e.g., between ribs), preferably at the margin of the innermost intercostal muscle and the membranous portion of the internal intercostal muscle. A location may be chosen that is proximal to the lateral cutaneous branch but at least 2 cm from the ganglia and 4 cm from the spine.

Approximately, 2-3 cm of the cryogenic surgical device 11 (including the distal tip 118) may be exposed, where the elongated shaft may be shaped with a curve for the costal groove. A hockey stick or C-shape may be used. The distal tip 18 of the cryogenic surgical device 11 may be placed directly on top of the nerve with a slight angulation that assures the nerve is directly under the distal tip 18. The insulated tube of the cryogenic surgical device 11 may be positioned on the rib and carefully slid down the rib until the cryogenic surgical device 11 falls off the rib into the costal groove.

Prior to ablation, the distal tip 118 may be pressed into the costal groove with enough pressure to create compression of the tissue for stability and reduced local perfusion. Adequate pressure may be pressure sufficient to create blanching if depressed against the skin. Post locating the distal tip 18 to contact the nerve or in close proximity thereto, cryogenic fluid flowing through the cryogenic surgical device 11 is operative to cool the distal tip 18 (to approximately −65C) and initiate or continue a freeze duration to freeze the nerve. By way of example, the freeze duration may be 120 seconds if the distal tip 18 is positioned in proximity to the nerve, whereas the freeze duration may be less (e.g., 90 seconds) in cases where the distal tip 18 is in direct contact with the nerve. The cryogenic surgical device 11 may be defrosted post freeze duration to allow disengagement between the distal tip 18 and the animal tissue. In exemplary form, as the cryogenic surgical device 11 defrosts, the distal tip 18 may turn bright and shiny and may be moved without resistance. To prevent tissue or nerve damage, the cryogenic surgical device 11 should not be forcibly moved while adhered to tissue. Post defrost, the freeze duration process and defrost sequence may be repeated at another location of the same nerve (or at a different location of a different nerve) and repeated as necessary to achieve the proper pain management result. In general, some exemplary cryoanalgesia procedures as described above may be repeated on the intercostal nerves located in each of the third to ninth intercostal spaces.

Following from the above description, it should be apparent to those of ordinary skill in the art that, while the methods and apparatuses herein described constitute exemplary embodiments of the present invention, the invention described herein is not limited to any precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A cryogenic device comprising:

an enclosed distal tip delineating a cavity in fluid communication with an egress orifice and an ingress orifice, where at least a portion of an exterior of the distal tip comprises a thermal application zone;

an exhaust conduit in fluid communication with the egress orifice;

a supply conduit in fluid communication with the ingress orifice, the supply conduit helically extending around at least a portion of the exhaust conduit proximal to the thermal application zone; and an insulating deformable wrap at least partially circumscribing and conforming to the supply conduit helically extending around at least the portion of the exhaust conduit to have a corrugated exterior and leaving exposed the thermal application zone.

2. The cryogenic probe of claim 1, wherein the distal tip includes a plug partially delineating the cavity, wherein the egress orifice and the ingress orifice extend through the plug.

3. The cryogenic probe of claim 2, wherein:

the plug includes a nipple extending away from the distal tip;

the deformable wrap circumscribes at least a portion of the nipple.

4. The cryogenic probe of claim 2, wherein the supply conduit extends through the plug via the ingress orifice and into the cavity.

5. The cryogenic probe of claim 2, wherein the exhaust conduit extends at least partially into the plug via the egress orifice.

6. The cryogenic probe of claim 2, wherein the distal tip includes a bulbous cap sealingly connected to the plug to delineate the cavity.

7. The cryogenic probe of claim 6, wherein the supply conduit extends through the plug via the ingress orifice and within boundaries of the bulbous cap.

8. The cryogenic probe of claim 6, wherein the exhaust conduit does not extend into the cavity.

9. The cryogenic probe of claim 1, further comprising a first actuator operative to vary spacing between first turns of a helix of the supply conduit within a first section.

10. The cryogenic probe of claim 9, further comprising a second actuator operative to vary spacing between second turns of the helix of the supply conduit within a second section of the cryogenic probe, where the first and second sections do not overlap.

11. A cryogenic device comprising:

an expansion cavity in fluid communication with an egress orifice and an ingress orifice, where at least a portion of the expansion cavity is in thermal communication with an exterior surface comprising a thermal application zone;

an exhaust conduit in fluid communication with the expansion cavity; and a supply conduit in fluid communication with the expansion cavity, the supply conduit helically extending around at least a portion of the exhaust conduit outside and proximal to the expansion cavity.

12. The cryogenic probe of claim 11, wherein the expansion cavity is at least partially delineated by an interface through which the egress orifice and the ingress orifice extend, the interface precluding fluid communication between the exhaust conduit and the supply conduit on a first side and allowing fluid communication between the exhaust conduit and the supply conduit on a second side.

13. The cryogenic probe of claim 11, wherein the expansion cavity is located at a distal tip of the cryogenic device.

14. The cryogenic probe of claim 13, wherein the expansion cavity is at least partially delineated by a bulbous projection.

15. The cryogenic probe of claim 14, wherein the supply conduit helically extends around at least a portion of the exhaust conduit within two centimeters of the bulbous projection.

16. A cryogenic device comprising:

an exhaust conduit in fluid communication with an expansion cavity;

a supply conduit in fluid communication with the expansion cavity, the supply conduit helically extending around at least a portion of the exhaust conduit; and an actuator operatively coupled to the supply conduit, the actuator repositionable along a range of travel to vary spacing between turns of a helix of the supply conduit, where varying the spacing between the turns of the helix of the supply conduit is operative to change the flexibility of the cryogenic device where the supply conduit helically extends around at least a portion of the exhaust conduit and is proximal to the expansion cavity.

17. A method of operating a cryogenic surgical device, the method comprising:

positioning a thermal application zone of an enclosed distal tip of a cryogenic surgical device proximate a target tissue, the distal tip delineating a cavity in fluid communication with an egress orifice and an ingress orifice;

cooling the thermal application zone of the distal tip by supplying a cryogenic fluid through the ingress orifice from a supply conduit helically extending around at least a portion of an exhaust conduit proximal to the thermal application zone while insulating at least a portion of the helically extending supply conduit using a deformable wrap at least partially circumscribing the supply conduit and leaving exposed the thermal application zone, the exhaust conduit in fluid communication with the egress orifice;

warming the distal tip by restricting flow of the cryogenic fluid through the exhaust conduit; and removing the distal tip from proximate the target tissue.

18. The method of claim 17, wherein positioning the thermal application zone of the enclosed distal tip of the cryogenic surgical device proximate the target tissue comprises placing the distal tip in direct contact with the target tissue.

19. The method of claim 17, wherein positioning the thermal application zone of the enclosed distal tip of the cryogenic surgical device proximate the target tissue comprises operating an actuator to vary spacing between turns of the helix of the supply conduit, where varying the spacing between the turns of the helix of the supply conduit is operative to change the flexibility of the cryogenic device where the supply conduit helically extends around at least the portion of the exhaust conduit.

20. The method of claim 17, wherein positioning the thermal application zone of the enclosed distal tip of the cryogenic surgical device proximate the target tissue comprises placing the distal tip proximate at least one of cardiac tissue and nerve tissue.

* * * * *